United States Patent [19]

Hansebout et al.

[11] Patent Number: 5,545,648
[45] Date of Patent: Aug. 13, 1996

[54] USE OF 4-AMINOPYRIDINE IN THE REDUCTION OF CHRONIC PAIN AND SPASTICITY IN A SPINAL CORD INJURED PATIENT

[75] Inventors: Robert R. Hansebout, Hamilton, Canada; Andrew R. Blight, Chapel Hill, N.C.

[73] Assignee: Canadian Spinal Research Organization, Ontario, Canada

[21] Appl. No.: 290,757

[22] PCT Filed: Dec. 20, 1993

[86] PCT No.: PCT/CA93/00554

§ 371 Date: Sep. 13, 1994

§ 102(e) Date: Sep. 13, 1994

[87] PCT Pub. No.: WO94/14439

PCT Pub. Date: Jul. 7, 1994

[30] Foreign Application Priority Data

Dec. 18, 1992 [CA] Canada .................. 2085785

[51] Int. Cl.$^6$ ............................................. A61K 31/44
[52] U.S. Cl. ............................................... 514/352
[58] Field of Search ................................... 514/352

[56] References Cited

U.S. PATENT DOCUMENTS 4,508,715  4/1985  Booth et al. ........................ 514/280
5,370,879  12/1994  Materson et al. .................... 424/490

FOREIGN PATENT DOCUMENTS 8909600  10/1989  WIPO .

OTHER PUBLICATIONS

Brain Res. Bull., vol. 22, No. 1, 1989, pp. 47–52, Andrew R. Blight 'Effect of 4–aminopyridine on axonal conduction--block in chronic spinal cord injury' cited in the application see abstract.

Soc. Neurosci. Abstr., vol. 13, No. 1, 1987, p. 62, A. R. Blight et al. 'Recovery of motor function in chronic experimental spinal cord injury enhanced by 4–aminopyridine', see abstract.

J. Neurosurg., vol. 63, No. 2, 1985, pp. 246–249, K. J. Burchiel et al. 'Effects of potassium channel–blocking agents on spontaneous discharges from neuromas in rats', see abstract.

Izv. Akad. Nauk. SSSR, Ser. Biol, No. 3, 1988, pp. 368–373, Lavretskaya et al., 'Potassium channels blockage an analgesic action of compounds' see abstract.

Medline database, abstract No. 89062841 & Farmacol. Toxicol. vol. 51, No. 4, 1988, pp. 32–34; Analgesic activity of pymadine, see abstract.

Eur. J. Pharmacol., vol. 106, No. 2, 1984, pp. 319–325, Pieter T. M. Biessels et al. 'Comparison of the pharmacological actions of some new 4–aminopyridine derivatives', see p. 319.

J. Neurotrauma, vol. 9, No. SUP1, Mar. 1992, pp. S211–S217, Russ Nockels et al. 'Pharmacological Strategies in the treatment of experimental spinal cord injury', see p. YA.

Current Opinion In Neurology And Neurosurgery, vol. 3, No. 2, 1990, pp. 208–212, L. W. Myers 'Therapy of multiple sclerosis', see p. 209, left column, paragraph 1.

Lemeignan et al, *Aminopyridines and Similarly Acting Drugs, Proceedings of IUPHAR Paris, France*, 1981, p. 323.

Mitsov et al., *Chemical Abstracts*, vol. 109, No. 13, abstract #104647b, 1988.

*Primary Examiner*—Marianne M. Cintins
*Assistant Examiner*—William R. A. Jarvis
*Attorney, Agent, or Firm*—Klauber & Jackson

[57] ABSTRACT

A method of reducing chronic pain and spasticity in a spinal cord injured patient by the administration of 4-aminopyridine is disclosed.

5 Claims, 5 Drawing Sheets

Subject GCh

FIG.4B

Subject EB

FIG.5

* Data not Recorded

USE OF 4-AMINOPYRIDINE IN THE REDUCTION OF CHRONIC PAIN AND SPASTICITY IN A SPINAL CORD INJURED PATIENT

This application is a 371 of PCT/CA93/00554 filed Dec. 20, 1993.

1. Field of the Invention

The present invention relates to the use of 4-aminopyridine (4-AP) in the treatment of neurological diseases. In particular, the=present invention relates to the use of 4-aminopyridine in spinal cord injured individuals to increase motor control and sensory ability and to reduce chronic pain and spasticity.

2. Background of the Invention

Neurological deficits resulting from traumatic injury to the spinal cord are traditionally ascribed to transection of axons in white matter pathways, which normally mediate interaction between regions of the neuraxis above and below the site of direct damage. Clinical pathological studies of spinal cord injury confirm that there is extensive loss of white matter, although the most severe damage usually occurs within central gray matter (Kakulas and Bedbrook, 1969; Jellinger, 1976; Kakulas, 1984). Complete transection of the spinal cord is relatively rare, but the extent of axonal survival is not usually determined, even in the small minority of cases where postmortem examination is performed. The completeness of the lesion is an important issue, however, since conduction failure in any surviving pathways may contribute to losses of sensory and motor function. Experimental studies in animals (e.g. Eidelberg et al., 1977; Eidelberg et al., 1981a; Eidelberg et al., 1981b; Blight, 1983a; Blight and DeCrescito, 1986; Bresnahan et al., 1987; Noble and Wrathall, 1989; Blight, 1991), and a very few clinical observations (Noordenbos and Wall, 1976) have shown that complex neurological functions can be mediated by a small proportion of surviving axonal pathways.

Electrophysiological recordings from isolated spinal cord have shown chronic failure of action potential conduction in surviving myelinated axons, following a blunt contusion injury (Blight, 1983b). Some of this conduction block can be overcome, at the level of single nerve fibers, using the drug 4-aminopyridine (4-AP) (Blight, 1989). Intravenous injection of this compound in animals with experimental or naturally occurring spinal cord injuries, produces significant improvements in electrophysiological (Blight and Gruner, 1987) and behavioral function (Blight et at., 1991). An initial study in spinal cord injury patients was organized by Dr. Keith Hayes, and indicated a potential for modest therapeutic benefit, mostly at the electrophysiological level, combined with a lack of serious side effects (Hayes et at., 1991 and submitted for publication).

SUMMARY OF THE INVENTION

In accordance with the present invention, a clinical trial was designed to examine the potential functional benefits of 4-AP in patients with chronic spinal cord injury: A placebo-controlled, double-blind, crossover design was used to allow for possible effects of patient expectation, and to minimize observational bias. A wide range of injury types were examined, based on the expectation that this approach to treating conduction failure would vary in its effectiveness with differences in the severity and distribution of damage to the spinal cord.

The results of the study demonstrated that 4-aminopyridine is useful in increasing motor control and sensory ability in spinal cord injured individuals. Surprisingly, 4-aminopyridine was also shown to reduce chronic pain and spasticity in certain individuals. The latter effect was unexpected based on the known properties of 4-aminopyridine.

Accordingly, the present invention provides the use of 4-aminopyridine in the treatment of a condition that affects the nervous system.

The present invention also provides the use of 4-aminopyridine to reduce pain, in particular in a spinal cord injured individual.

The present invention also provides the use of 4-aminopyridine to reduce spasticity, in particular in a spinal cord injured individual.

The present invention further provides a commercial package, containing as active ingredient, 4-aminopyridine, together with instructions for the use thereof to treat a spinal cord injured individual, in particular to reduce pain or spasticity.

DETAILED DESCRIPTION OF A PREFERRED EMBODIMENT

Preparation of 4-aminopyridine (4-AP)

The drug was obtained in purified powder form from the Regis Chemical Company (Morton Grove, Ill.) and prepared as an injectable solution, using a 0.9% saline vehicle (Uges and Huizinga, 1981), by the pharmacy of St. Joseph's Hospital. The pharmacy was also responsible for testing pyrogenicity, randomizing the order in which drug and vehicle were administered to different patients, and for providing an escalating scale of dosage during the course of the study. The 4-AP for the first two patients was prepared at a concentration of 3 mg/ml, and the concentration was increased to 4 and 5 mg/ml for succeeding subjects (see Table 1). The drug was further diluted by a factor of 50 times in dextrose saline before delivery, and was administered in the form of a continuous intravenous infusion at a rate of 150 ml/hr controlled by a peristaltic infusion pump. Therefore the delivery rate of the drug increased from 9 mg/hr in the first two patients to 15 mg/hr in the last four. Total intended dosage ranged from 18 to 30 mg. The vehicle control was indistinguishable from the drug solution and was delivered in an identical manner.

Subjects

The eight patients enrolled in the study were selected to provide a range of spinal cord lesions, including cases of quadriplegia, quadriparesis, paraplegia and paraparesis. The chief exclusion criteria in selection of patients were: evidence of mental incompetence; infectious disease; previous head injury or brain damage; history of epileptic seizures or lowered seizure threshold; cardiovascular, metabolic, kidney or respiratory abnormalities; known allergy to pyridine containing compounds; and pregnancy. Five male and three female patients were involved, ranging in age from 18 to 65 years of age. All were chronic cases, 1.5–10 years from the time of injury. Seven were traumatic injuries and one was a case of transverse myelitis of unknown origin. A more complete description of the patient histories and associated drug dosage is given in Table 1.

All but two of the subjects (HT,GCh) were under medication for pain and/or spasticity. These patients were required to suspend any regular medication for the duration of the experimental treatment and evaluation, with a suitable washout period before the study began. The study was approved by the Institutional Committee on the Use of Human Subjects and the Health Protection Board of Canada. All subjects were informed of the potential risks of the experimental study and each provided informed consent.

Protocol

The experimental design was a double-blind, placebo-controlled, crossover study in which each patient was administered the drug and a vehicle control on different occasions, separated by two weeks. The order of delivery was randomized. The randomization code was held independently by Pharmacy personnel and was not revealed to the investigators until after tabulation and analysis of the data.

The schedule of each trial was the same. The patient was admitted to the hospital on the preceding day and in the early morning was assessed by neurological examination and electro-diagnostic evaluation. Administration of the drug or placebo, through an in dwelling venous catheter, was then begun and continued for approximately 2 hours, arranged in 20 minute sequences based on delivery of 1 ml aliquots of the 4-AP solution. The patient was monitored electroencephalographically at frequent intervals throughout the procedure. Samples of blood and urine were obtained from an additional intravenous catheter and from the urinary catheter respectively. Blood was obtained at intervals up to 5 hours from the beginning of drug delivery and urine obtained pre-infusion and at 1 and 2 hours after the beginning of infusion. The patients were re-evaluated by complete neurological examination, by the same examiner, at the end of the period of drug delivery. They were then re-examined with the electrodiagnostic tests. A more limited neurological examination was sometimes performed during drug delivery in an attempt to identify any early changes, without producing significant testing fatigue. The electrodiagnostic tests were repeated at 2 hours after the cessation of drug delivery. Patients showing apparent effects of the treatment remained in the hospital overnight and were examined on the following day. Subsequent contact with the patients was by telephone interview or as a result of their correspondence regarding longer term changes associated with their treatment.

Two of the patients who reported more prolonged effects of the drug were returned to the hospital after 4 months for a second, unblinded trial, which included neurological examinations daily for 3–4 days. Plasma samples were also obtained daily from these two patients, for measurement of 4-AP.

Electrodiagnostic testing

Immediately before and after the infusion of 4-AP or placebo, and at approximately 2 hours after the end of the infusion, patients were evaluated with a set of standard electro-diagnostic tests: conduction in peroneal, posterior tibial and sural nerves, electromyography of tibial is anterior and gastroc-nemius muscles during rest and maximal voluntary contraction, and somatosensory evoked potentials. Patients were also monitored with electroencephalography, at intervals during the infusion, to look for evidence of potential for seizure activity.

Neurological Evaluation

Patients were evaluated using a modified form of the American Spinal Injury Association (ASIA) Standards for Neurological Classification of Spinal Injury Patients (revised 1990). The modifications were mainly required to simplify the examination so that it could be performed on patients lying on a bed with intravenous catheters, electrodes and urethral catheters restricting the range of motion. Examinations performed after the day of drug delivery were made on an outpatient basis with the subjects partially clothed, and evaluation of dermatomes was sometimes incomplete. Each part of the examination was videotaped for later review and was repeated on the two sides of the body.

Grading of motor abilities was made on the ASIA 0–5 point scale wherever possible:

0—absent (total paralysis)

1—trace (palpable or visible contraction producing little or no movement around joint)

2—poor (active movement through much or all of the normal range of motion, with gravity eliminated— where relevant)

3—fair (active movement through full range of motion against gravity)

4—good (active movement against resistance)

5—normal.

The muscles examined included: deltoid, biceps, triceps, wrist extensors, wrist flexors, finger flexors and extensors (combined), hip flexors (iliopsoas), hip extensors, quadriceps, hamstrings, ankle dorsiflexors (tibiails anterior) and plantarflexors (gastrocnemius, soleus), and toe extensors (extensor hallucis longus). The total possible score for the full motor examination was 130.

Sensory abilities were graded on an analogous 0–4 point scale:

0—absent (no ability to detect the stimulus)

1—trace (patchy or variable ability to detect stimulus with little or no resolution of quality)

2—light (able to detect stimulus but much weaker, or of altered quality relative to equivalent unaffected areas)

3—moderate (able to detect stimulus with practically full quality but reduced intensity)

4—normal in quality and intensity of sensation.

The sensory modalities tested were light touch, pinprick, vibration, joint position, and temperature. The dermatomes tested for touch and pinprick were: C5,6,7,8, T1,T7–9,L1, 2,3,4,5, and S1, giving a total possible score of 96 for each modality. Vibration sensation was usually tested bilaterally, at the shoulder, elbow, knee and ankle. Temperature sensation was tested, with the subject's eyes closed, by blowing cool air from a distance or breathing warm air in close proximity on the dorsal surface of the hands and feet. Joint position sense was examined with the subject's eyes closed, by imposed flexion and extension movements of the thumb and great toe. The total possible score for the full sensory examination was 256 points.

Segmental reflexes (biceps, triceps, knee- and ankle-jerk) were evaluated in the conventional manner with a reflex hammer and scored on a 0–4 point scale:

0—no detectable response

1—weak response

2—brisk response of normal amplitude

3—abnormally large amplitude response

4—large amplitude response with some clonus.

The total possible score in a patient with hyperreflexia and clonus in all tested muscles was 32.

Measurement of 4-AP in plasma and urine

Samples of blood were collected from an in dwelling venous catheter in the arm opposite that into which the drug was delivered. Ten or eleven such samples were obtained at intervals up to 5 hours after the initiation of drug delivery (see FIG. 1). Urine samples were withdrawn from the patients' urinary catheter bags at 1 and 2 hours after the initiation of drug infusion.

Plasma and urine samples were stored at −80° C. until 4-AP levels were analyzed by means of column liquid chromatography, according to a technique described in detail elsewhere (Kostka et al, 1992). Briefly, both plasma and urine samples were subjected to benzoylation by the Schotten-Baumann reaction to convert 4-AP to N-benzoyl-4-AP (Bz4-AP) prior to liquid-liquid -extraction. Propionyl procainamide (PPA) was chosen as the internal standard. These extracts were chromatographed on a 15 cm×4.6 mm ultra-sphere octyl column using a mobile phase containing 12% aceto-nitrile and 2 g/L tetramethyl ammonium perchlorate adjusted to pH 3 with perchloric acid. The extraction recovery of Bz4-AP was 80–85%.

RESULTS

The study was performed according to the established protocol, with a few exceptions. One patient (AW) received only 25 mg 4-AP rather than the planned 30 mg total dose. Infusion was suspended in this case because of a combination of discomfort in the arm at the site of infusion, and a significant degree of agitation and anxiety expressed by the patient. There were no further complications in this case and the patient returned to a more comfortable condition within less than an hour of suspending the infusion. One patient (LJ), expected to receive 18 mg of 4-AP in 6 doses of 3 mg, was not available on the first day of the trial, and was not studied until the dose had been raised to 5 mg. Since the pharmacy had prepared a smaller amount of the material for injection, this subject could only be given 5 doses of 5 mg. One patient (RB) was unable to maintain suspension of his normal pain medication (Percocet-oxycodone HCl, acetaminophen) and was allowed to resume on the day of the test.

Three patients receive the placebo and five received the 4-AP in the first trial (Table 1). The pharmacy did not release the information on the drug or placebo status of the infusions to the investigators until all the data had been evaluated, including the chemical analysis of blood and urine samples, which was the last information to become available.

Plasma levels of 4-AP

Figure 1A:
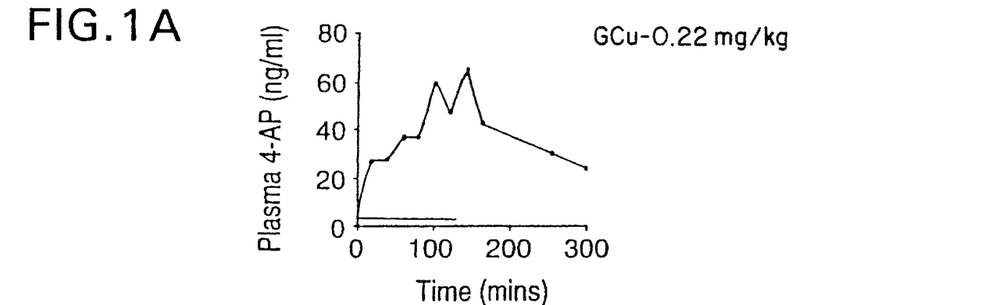
FIGS. 1A–1H show graphs illustrating the time course of changes in the plasma levels of 4-AP in all subjects, in ascending order of total dose. Most subjects showed some degree of oscillation of the measured drug levels, perhaps indicative of entero-systemic recirculation. The period of 4-AP infusion is indicated by the solid bars.
Figure 1B:
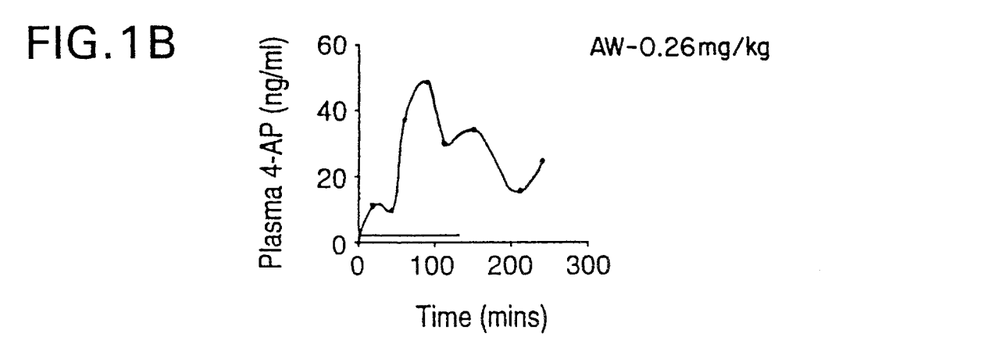
Figure 1C:
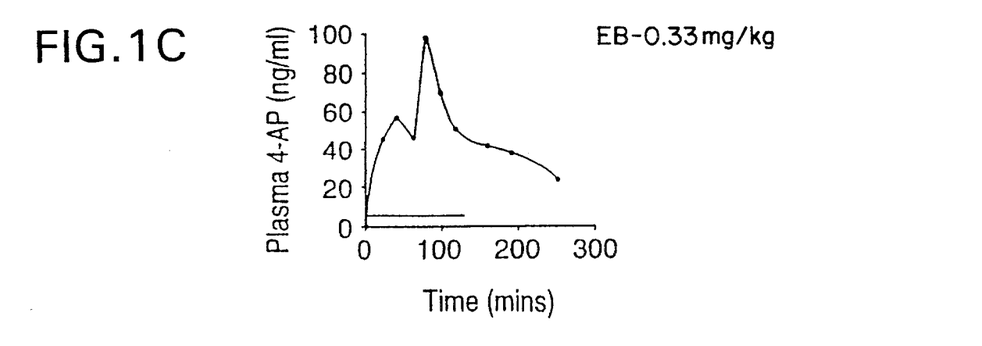
Figure 1D:
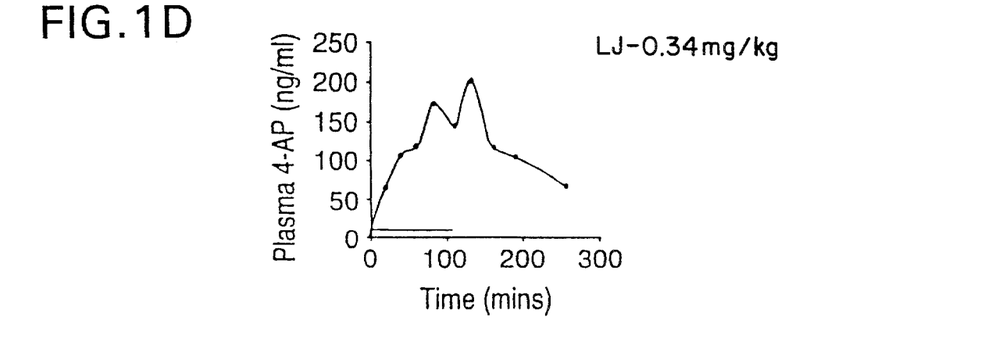
Figure 1E:
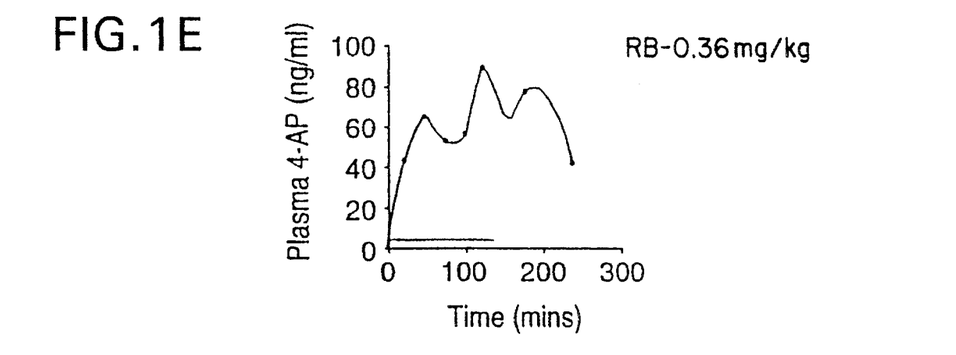
Figure 1F:
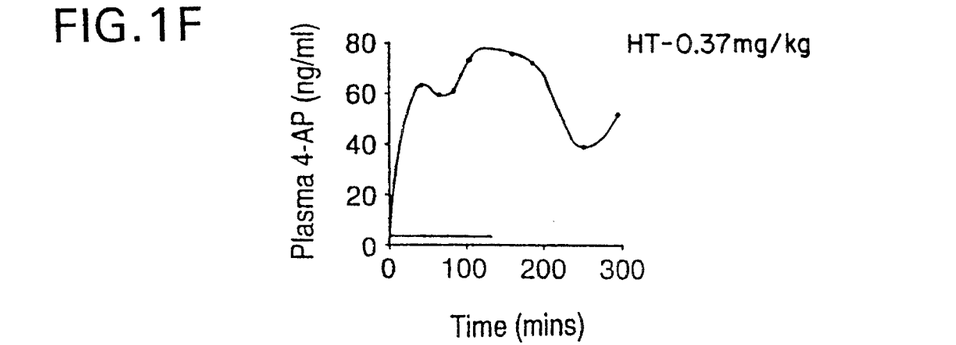
Figure 1G:
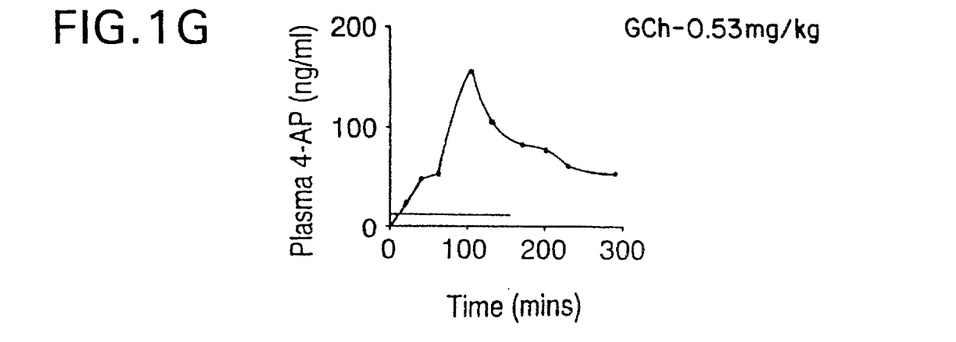
Figure 1H:
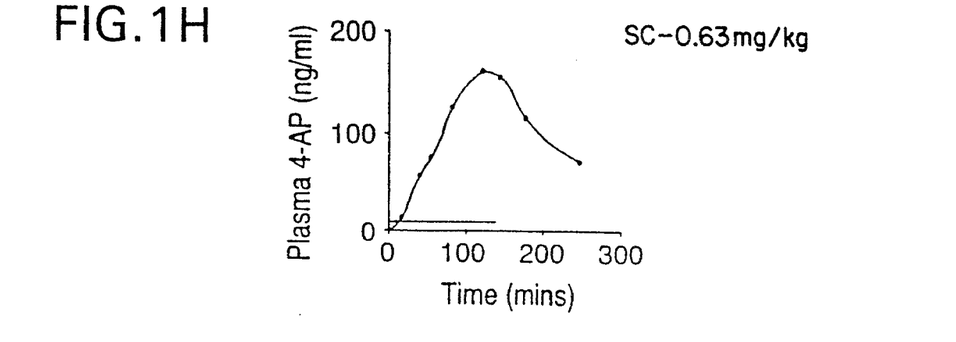
Figure 2:
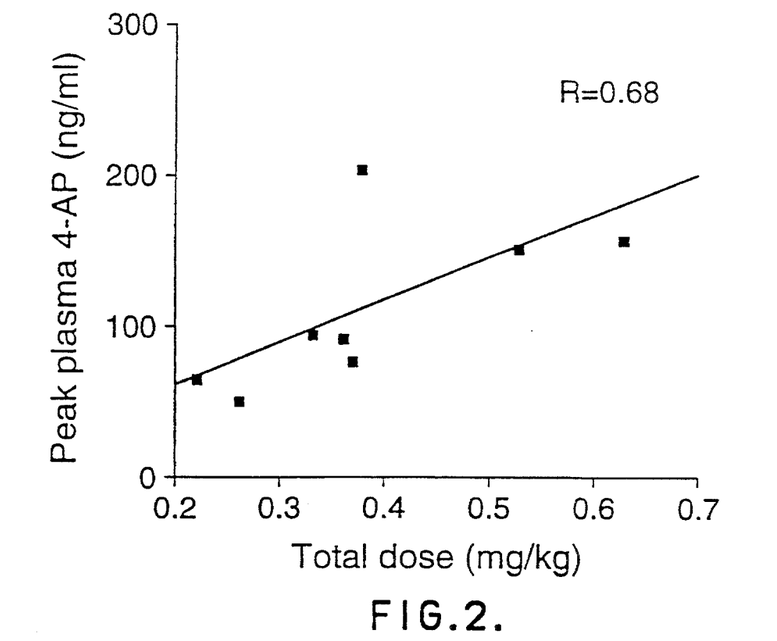
FIG. 2 is a scatterplot to show the correlation between the administered total dose of 4-aminopyridine (in mg/kg) and the peak plasma levels measured. The observed relationship (least squares regression) is such that for each mg/kg infused over approximately 2 hours, the peak plasma level achieved was approximately 0.27 mg/l.
Figure 3:
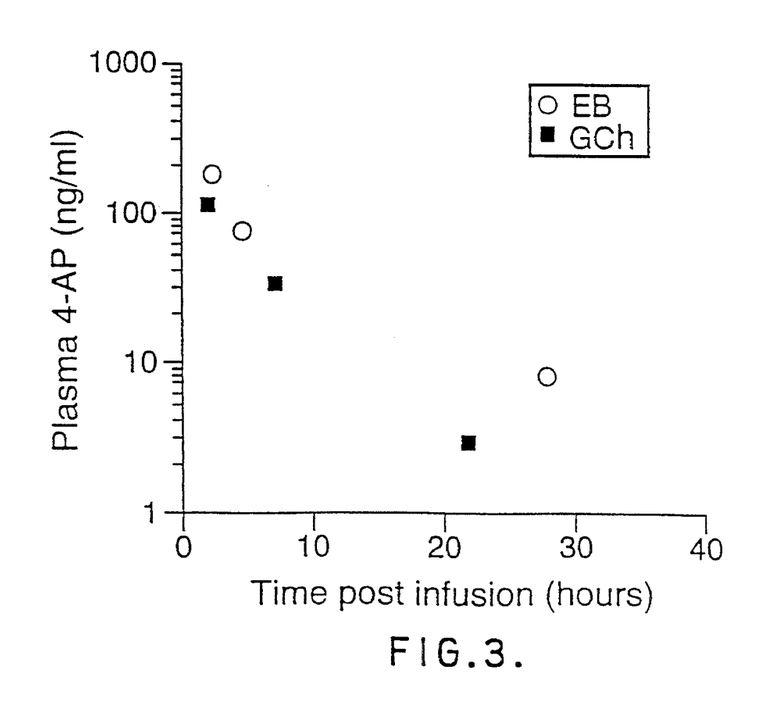
FIG. 3 is a graph of the plasma levels of 4-AP recorded in two subjects (EB,GCh) following their second, unblinded administration of 4-AP. Plasma levels were below the limit of detection (c. 3 ng/ml) by 48 hours in both patients.

The time course of changes in plasma levels of 4-AP in each of the subjects is shown in FIGS. 1A–1H. Most subjects showed oscillation in the measured drug levels. Peak levels in the circulation occurred slightly before or after the end of the infusion period. The peak plasma level recorded correlated significantly with the dose administered to the patients in mg/kg/hr (FIG. 2). All the subjects showed significant plasma level of 4-AP at 2–3 hours after the end of the drug infusion, when the last blood sample was obtained, and it was not possible to extrapolate from this data a likely time course of drug elimination. Blood samples were taken daily for 3 days from the two subjects who returned for a second, unblinded administration of 4-AP. The plasma levels recorded on the day of infusion and the day after infusion are shown in FIG. 3. 4-AP concentration was below the level of detection (c. 3 ng/ml) in the samples taken 2 days after administration. The rate of decline of plasma drug concentration in these two patients indicates that there would be less than 1% of the peak levels in the circulation by 2 days after the infusion.

Negative side-effects

The most frequently detected side effect of the drug was discomfort in the arm in which the drug was infused. The intensity of discomfort varied in different patients from no more than that normally experienced with an intravenous catheter (comparing with that present in the contralateral arm for blood sampling) to aching and burning pain sufficiently strong to require suspension of drug delivery in one patient. Three of the subjects (HT,GCu,GCh) reported no unusual sensation in the arm or any other negative side effects. Two of the patients (RB,AW) reported severe burning and aching in the arm and both these patients also experienced heightened anxiety, accompanied by short, alternating episodes of sweating and shivering, towards the end of the infusion period. Both these patients were marked by volatile personalities and one (RB) by significant generalized anxiety before the trial. The other subject (AW), the only one who could not complete the infusion phase of the drug trial, also became impatient and refused to complete the electrodiagnostic phase of the placebo trial. Two subjects (LJ,EB) reported a feeling of light-headedness towards the end of the infusion period. Two patients (AW,EB) reported delayed burning sensations in areas of skin below the level of injury, lasting for 1–2 hours, during the night after the infusion. No other obvious side effects of the drug were detected in the course of the study. No adverse indications were detected on the electroencephalographic recordings, nor in the routine monitoring of vital signs.

Electrophysiological effects

Six of the subjects showed no detectable somatosensory evoked potentials in response to posterior tibial nerve stimulation either before or after injection of the drug. The remaining two subjects (AW,GCh) showed small amplitude, but repeatable, somatosensory evoked potentials. These did not change significantly in form or amplitude following infusion of 4-AP or placebo. No consistent effects on peripheral nerve conduction were detected. The electromyographic data were consistent with observed changes in strength of muscle contraction, but were too limited in number of samples collected to be confident of the underlying variability of the recording.

Neurological effects

No subjects reported any beneficial changes following injection of the saline vehicle. Three subjects (RB,SC,HT) also noticed no improvement in their condition following infusion of the 4-AP. These were three of the most severely injured patients and included the two subjects diagnosed as Frankel class A—no motor or sensory function below the level of the lesion, and one of the two patients diagnosed as Frankel class B. The remaining 5 subjects, with a range of "incomplete" injuries showed motor and/or sensory effects, some of which were detected on the scheduled neurological examination on the day of infusion. Later effects were reported by the patients themselves, and prompted a more detailed examination of the time-course.

Changes in the neurological examination at 2 hours

Some changes in neurological score were noted in patients at 2 hours after the start of infusion of vehicle and drug. The total number of points difference in the pre-infusion and post-infusion examinations are shown in Table 2. Though the examiners assigned half point scores in cases where they felt that subjects fell between score categories, any half point differences between pre- and post-infusion scores have been ignored in this analysis. Also omitted from this tabulation are the scores for vibration sensation, which are shown separately in Table 3. The most striking changes in score were clearly those following 4-AP administration, and some of these changes will be examined individually below. In almost all cases the various categories of evaluation showed similar or higher scores following 4-AP administration, whereas scores tended to stay the same or decrease in the placebo trial (Table 2). The exception to this trend was found in vibration sensation, where scores in three subjects decreased substantially after 4-AP infusion (Table 3).

The overall changes in motor and sensory score, derived from Table 2, were compared between the placebo and 4-AP trial using the Wilcoxon matched pairs test. The change in sensory score Was significantly greater following 4-AP (p=0.03), the change in motor score was not (p=0.08), given this small number of cases.

There was a marked tendency for increase in amplitude of deep tendon reflexes immediately after infusion of 4-AP, compared with relatively little variation following the placebo administration (Table 4). The increase in reflex score occurred predominantly in the arms, probably because the lower limb scores were already at the maximum value of 4 before drug administration. The two patients (EB,GCh) examined at longer intervals showed slight reductions in deep tendon reflex scores at 24 and 48 hours after infusion, consistent with their reduction in spasticity. Two other patients examined at 24 hours after drug administration (AW,LJ) also showed reduced reflex responses at that time, despite maintained effects on motor and sensory function.

Later changes in the neurological examination

Neurological examination at 24 hours after administration of the drug was not a requirement in the original protocol, and five patients left the hospital on the day of administration. Three subjects examined on the day after receiving 4-AP (LJ,AW,GCh) showed sustained improvements in neurological function, including in one (LJ) a striking improvement of pinprick sensation and joint position sense below the lesion that was not seen at 2 hours. These findings, together with the reports from other patients of sustained or delayed changes in function lead to a second evaluation of the effects of 4-AP in two subjects, with daily re-examination until neurological changes were largely extinguished (see below).

Delayed changes reported by the subjects

The initial study was designed to examine effects that would be reversed by the day after drug infusion, based on the published pharmacokinetics of 4-AP and reports of other clinical experience with the drug. However, the five patients with less complete injuries all reported some delayed or prolonged effects during the days after they had received the 4-AP. These reports were sufficiently complex to be considered individually:

Subject LJ

This patient reported increased sensation, pain in the left arm, and some nausea and light-headedness during and immediately after the infusion. The next day he felt there was slightly greater movement in one thumb and index finger. He also felt there was more sensation below the level of injury, and this was confirmed by the neurological examination. The usual burning pain he experienced in his buttocks was absent, though there was still some burning in his lower limbs, which had increased compared with before the study. Subsequent medical observations were complicated by the occurrence of a urinary tract infection.

Subject EB

The subject reported no effects of the first infusion (placebo). Following the second infusion, the subject chose to go home immediately after the study was completed. She felt that her lower limb muscular spasms were so severe on the day of the trial that it had been difficult to evaluate her motor performance. The day after drug delivery there was a "remarkable return of sensation below the level of the injury to virtually normal sensation on both sides". There was also a marked reduction in spasticity for the three days following the infusion. The patient only returned to her normal requirement for Baclofen on the fourth day. This reduction in spasticity was accompanied by increased motor power in the left arm and leg. The fingers of the left hand, normally capable of only a few flickers of movement, could be moved back and forth 20–30 times, in contrast to the usual rapid fatigue. A similar improvement was seen in right ankle movement. Possible side effects included a "warm sensation under the skin from neck to back" for two days and an episode of constipation. This patient returned for more detailed evaluation of long term effects in a second, unblinded trial.

Subject GCh

This patient showed marked improvement in sensation below the lesion during the course of the 4-AP infusion. He reported that he suffered no negative side effects and that his legs felt "more normal". His legs usually felt cold to him, and there was persistent pain in his feet and legs. For at least 2 days after the drug infusion the pain in the legs was absent, though it remained to some extent in his feet, and his legs felt warm, both "internally" and to the touch. By 3 days after the infusion he had returned to his usual state. Increased motor power in this patient expressed itself mainly in a greater endurance. Usually, he would have difficulty making repetitive movements of his toes, but on the day of 4-AP infusion he was able to move them back and forth many times without the usual fatigue. This increased motor capacity was also associated with a decrease in spasticity.

He returned for a second, unblinded trial of 4-AP and experienced essentially the same effects, with increased sensation and motor endurance below the level of the injury, reduction of chronic pain, and marked reduction in spasticity. Muscle spasms of the legs were quite severe before the second infusion. After infusion and for more than 24 hours afterwards, spasticity was so markedly reduced that the patient found unusual difficulty in making wheelchair transfers, because his legs would not act to support him in the accustomed way.

Subject AW

This patient showed increased strength in the lower limbs after as little as 8 mg of the 4-AP infusion. He also noticed a marked improvement in breathing, being able to use chest expansion rather than diaphragm breathing. After 21 mg of the infusion, his arm became quite painful and he became anxious, then angry, and began to show alternative bouts of sweating and shivering. Drug infusion was stopped and the subject returned to a more comfortable state in about 10 minutes. He was aware of more sensation and strength in his legs, though this appeared to be less than during the earlier part of the infusion. The morning after the infusion, he showed improved strength and sensation in his legs, was able to stand more rapidly and easily from his wheel chair, and was very positive about the overall effects of the drug. He reported, on his return for the second administration 2 weeks later, that the motor and sensory effects, including improved breathing had lasted about 2 days, and then gradually faded.

Subject GCu

This subject was the least severely injured. He did not notice any changes in his status on the day of infusion, but later reported that the day after the drug infusion his arms and right leg had been stronger, by "perhaps about 25%" and he could deal more effectively with his farm work. He also felt a significant reduction in the usual tingling paresthesia in his hands.

Second unblinded administration

Figure 4A:
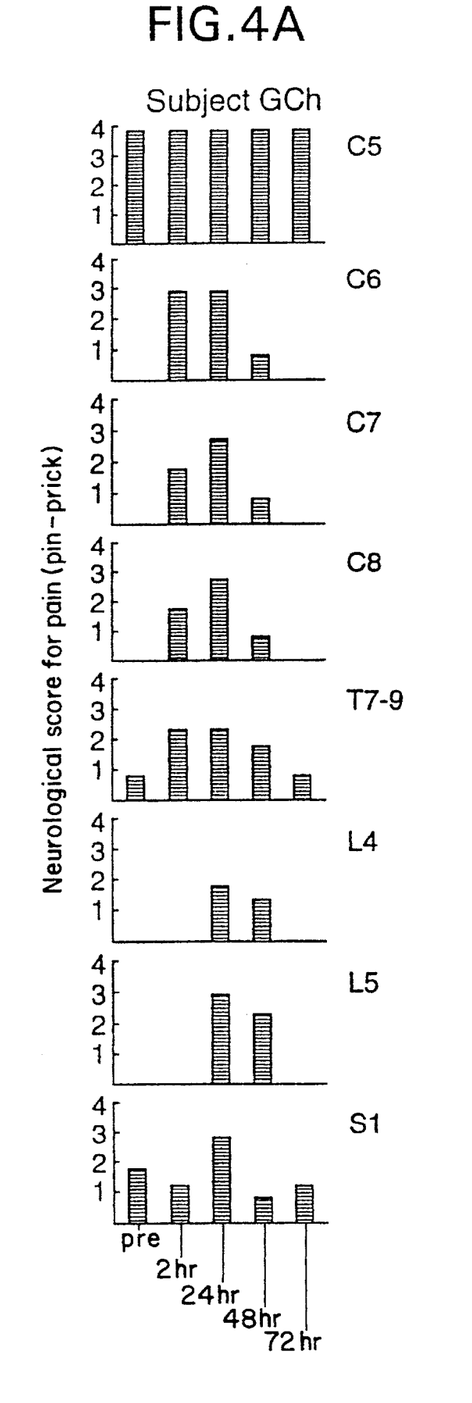
FIGS. 4A and 4B show histograms to illustrate the sequence of changes in the neurological score for pin-prick sensation in the two subjects (GCh and EB) who returned for a second trial. Average scores for left and right side are shown for the tested dermatomes between C5 and S1. The maximal improvement in sensory score for both subjects was obtained at 24 hours after infusion of the drug. The patient examined at 72 hours (GCh) had returned completely to pre-infusion status.
Figure 4B:
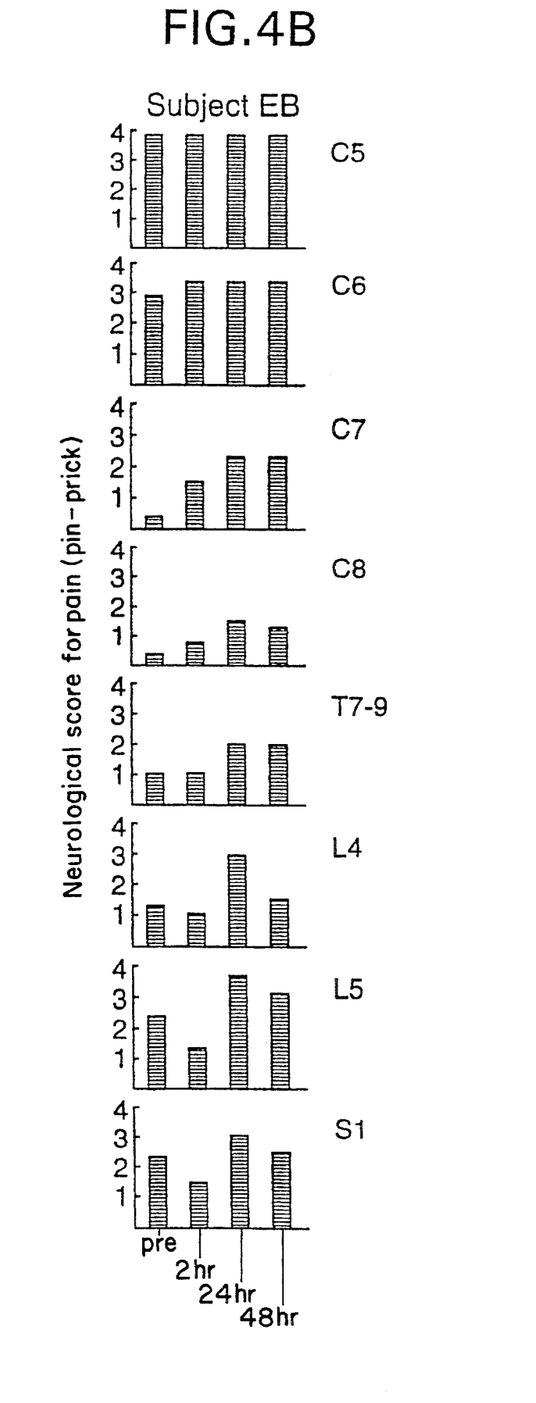

The two patients returning after 4 months for a more prolonged evaluation (GCh,EB) showed effects and side effects similar to those seen in the earlier, blinded administration of 4-AP. On this occasion, the time course of reversal of the effects could be examined more closely. The most striking and widespread change in the neurological status of both patients was the distribution of pinprick sensation below the level of injury. A remarkable increase in the response to pinprick stimulation below the level of injury is shown graphically in FIGS. 4A and 4B. The improvement in sensation appeared to peak at 24 hours and was still detectable at 48 hour post infusion in both cases. The effect seemed to be entirely reversed by 72 hours in the one subject who was examined at that time. There was some indication of a proximodistal delay in the onset of effect, including, an initial depression of response in the most distal dermatomes, examined at 2 hours after infusion.

Figure 5:
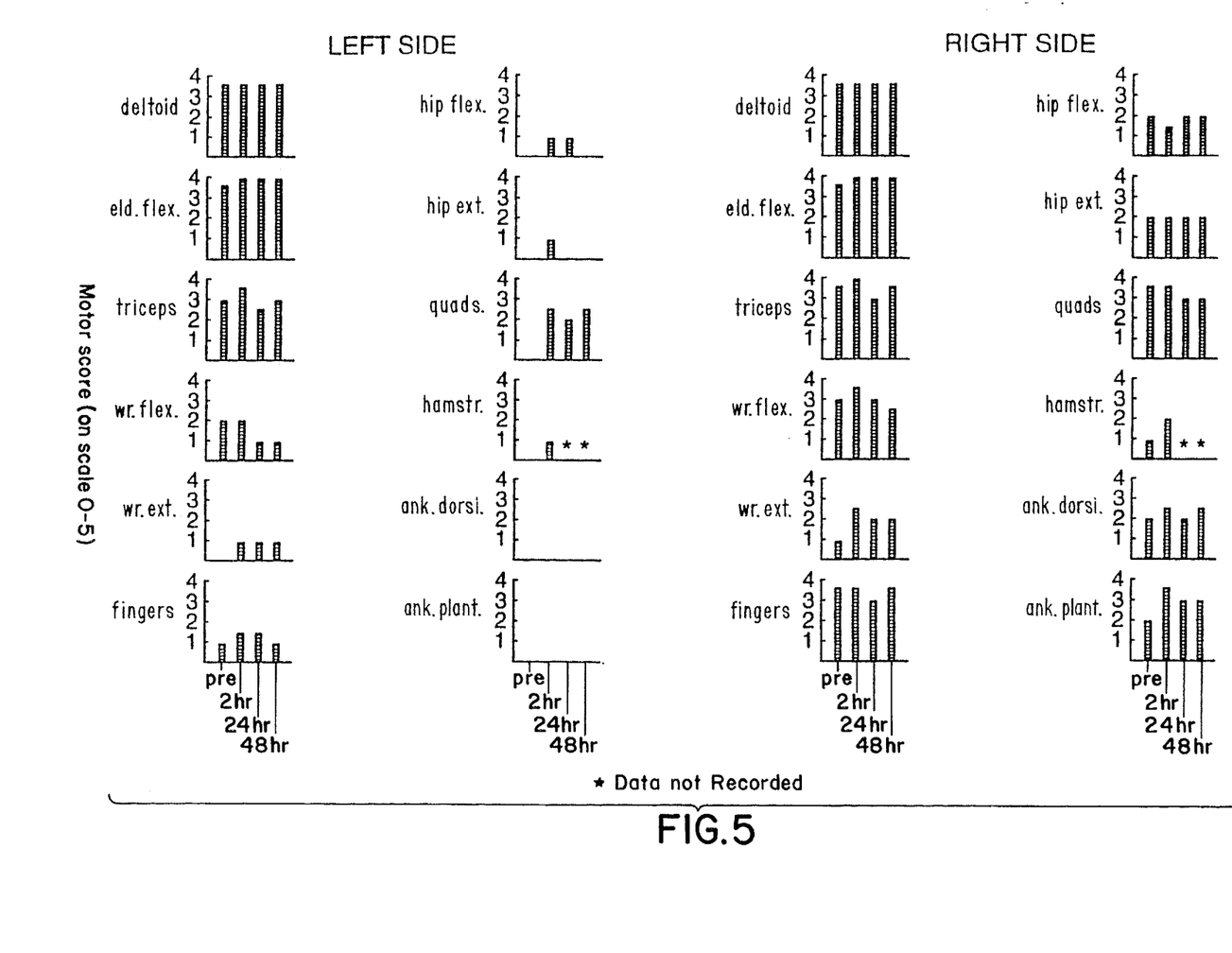
FIG. 5 shows histograms to illustrate the sequence of changes of motor score in the tested muscles on the two sides of the body in one of the subjects (EB) who returned for a second infusion of 4-AP. As in the sensory examination (FIG. 4) increases in score were sustained at 24 hours after infusion, though the maximal improvement appeared in this case to be already present at 2 hours.

The examination of motor abilities was complicated by variations in spasticity before 4-AP administration, as well as the sometimes conflicting effects of the drug on motor control and motor power. A reduction in the spasticity of leg muscles led at times to a reduction of motor power, especially in movements at the hip and knee, where a patient is often able to use the background rigidity of the muscle as an aid to movement. The data that is available, points to a prolonged time course of effect on motor systems similar to that seen in the sensory evaluation. However, there was some indication that the peak effect on motor function was achieved by the first examination at 2 hours (FIG. 5).

DISCUSSION

This study has shown that moderate doses of 4-AP administered to chronic spinal cord injury patients are associated with a range of beneficial effects in a significant proportion (5 of 6) of those with "incomplete" were seen in this group of patients than in previous studies.

The objectivity of the neurological effects is supported by several factors. First, the study was double blind, and though some subjects and the investigators may have been effectively un-blinded on the active drug trial by the presence of side-effects, there was no relation between the appearance of side-effects and apparent benefit. The most widespread and strongest effects were obtained in a patient without side-effects, and no benefit was detected in two subjects with side-effects. The effects reported by the patients were not always those they had been lead to expect as possible. Some of them were also surprising to the investigators, particularly the reduction in pain and spasticity, yet these were reported independently by patients not in communication with each other.

Statistical evaluation of these changes is made difficult by the small number of cases, by their selection from a wide range of injury intensities, and by the ordinary scoring used in the neurological analysis. These limitations should be weighed against the reversibility of the drug effect, its repeatability in the two patients examined a second time, and the properties of the effects shared between subjects. The benefit derived from the drug appeared to be related to the severity of injury, with the greatest effects in moderately severe quadriplegia (Frankel class C). Two patients with neurologically "complete" spinal cord lesions showed no beneficial effects. The small changes in neurological score that followed placebo administration in some subjects (Table 2, 3) are likely to be the result of three principal factors: 1) fatigue induced by repeated testing and the prolonged immobility required by the study itself; 2) limitations in the repeatability of score assignments; 3) actual variations in the neurological function of the subjects, including the existence of "patchy" receptive fields within tested dermatomes. The first of these factors is likely to be the most dominant, and probably accounts for the preponderance of negative changes following placebo administration. The smaller number of negative changes following 4-AP administration should be taken into account in addition to the greater number of positive improvements in score.

The observation that 4-AP administration may have some negative effect on vibration sensation (Table 3) is intriguing. Though the sample size was small, the possibility that this reduction in vibration sensation was actually an effect of 4-AP was supported by the observation that two of the subjects (EB,GCh) also showed some reduction in vibration score on a repeat, un-blinded injection of the drug. It seems feasible that blockade of potassium channels may selectively affect the transmission of signals related to high frequency, low amplitude stimulation.

Neurological Effects in Spinal Cord Injury

Although, some of the neurological changes associated with administration of 4-AP in this group of spinal cord injured patients were similar to those seen previously in patients with multiple sclerosis (Stefoski et al., 1987; Davis et al., 1990; Stefoski et al., 1991), including selective increases in motor strength and recovery of sensory deficits with a relatively rapid onset, the duration of the changes was surprisingly long, including some subjects with improved function extending over 48 hours. Such changes occurred to variable degree in 5 of the 6 cases of incomplete spinal cord injury. The benefit was sufficiently apparent to the patients themselves that four of the patients expressed a strong desire to be able to receive the drug on a regular basis.

Some of the most intriguing effects, seen in both complete and incomplete cases include long lasting reductions in spasticity and in chronic pain and dysesthesias relating to skin temperature in the lower extremities. These results are supported by a number of factors: a) the subjects were not led to expect such long term effects, but were specifically told that any potential benefit would last at most for a few hours; b) patients independently reported similar combinations of changes that neither they nor the investigators expected (and actually ran counter to the expectation that 4-AP might make spasticity and paresthesias worse); c) these changes were reported only following drug administration and not after placebo administration; d) such changes resulted in greatly reduced usage of analgesic in one case and antispastic medication in at least two cases e) the effects were reproduced by a second administration of the drug 4 months later in two of the subjects.

There appeared to be two possible explanations for the long duration of effects: either the elimination of drug was delayed in these spinal injured subjects, beyond what has been seen in normal volunteers and multiple sclerosis patients (Uges et al., 1982; Evenhuis et al., 1981; Stefoski et al., 1991), or else the drug elicits secondary changes in the nervous system that lead to prolonged reduction of spasnicity and abnormal pain sensation. The first possibility was strengthened by the previous observations of decreased clearance of drugs in spinal cord injury patients (Segal et al., 1991) and was tested by examining the plasma level of 4-AP over the course of 3–4 days from the time of injection in two subjects showing prolonged effects of the drug. Though there were detectable levels of the drug in the plasma the day after infusion, the time course of elimination clearly did not correlate with the prolonged neurological effects that were seen on examination and reported by the patients. This indicates that the 4-AP indeed initiates changes in the nervous system that are self-sustaining for a period of 1–2 days.

Pain and Spasticity

The mechanism of effect on chronic pain and spasticity is difficult to assess, though the importance is critical, given the high incidence of these problems and the intractable nature of central pain in the context of spinal injury (Beric et al., 1988; Tasker, 1990). The anatomical substrates and physiological mechanisms of chronic pain in spinal cord injury are not well understood (Beric, 1990; Kakulas et al., 1990; Xu et al., 1992). One of the contributing cellular mechanisms may be that injured and demyelinated nerve fibers tend to become spontaneously active (Ochoa, 1982; Smith and McDonald, 1982). Blockade of potassium channels by 4-AP tends to produce or enhance such spontaneous activity and to elicit "burst" (multiple action potential) responses to electrical stimulation in injured nerve fibres (Waxman et al., 1985; Targ and Kocsis, 1986; Kocsis et al., 1986; Blight, 1989). It was expected, therefore, that 4-AP might increase the intensity and incidence of chronic pain and dysesthesias.

Similarly, since 4-AP at relatively high concentrations is known to enhance synaptic transmission in the spinal cord (Lemeignan, 1972; Jankowska et al., 1977; Jankowska et al., 1982), it was expected that spasticity might be increased, together with the overall excitability of the nervous system. In fact application of the drug was associated in some cases with a relief of chronic pain and spasticity, so it is possible that other, more specific effects of potassium channel blockade dominate over generalized increases in excitability. Also, it appeared from the changes in deep tendon reflex amplitude that generalized enhancement of synaptic transmission was more prevalent on the day of drug administration and waned more rapidly than the specific changes in sensory and motor function.

Three subjects who suffered from chronic, painful dysesthesias below the level of the lesion (GCh,GCu,LJ) reported considerable relief following 4-AP infusion, predominantly proximal in the limb. One subject (EB), who experienced dysesthesia in the form of a persistent itch in one shoulder, reported no change in this condition following administration of the drug.

SUMMARY

The above results indicate that 4-aminopyridine can increase motor control and sensory ability and reduce chronic pain and spasticity spinal cord injured individuals. The latter two effects have not previously been reported. Although the study was restricted to spinal cord injured individuals, 4-aminopyridine may also be useful in treating other conditions that affect the nervous system, in particular to reduce pain and spacticity in such conditions.

Although 4-aminopyridine was administered intravenously in the present study, it is expected that oral administration would also be useful and may remove the side effect encountered in the present study which was pain the arm around the site of infusion.

TABLE 1

Characteristics of subjects and 4-aminopyridine dose administered.

| SUBJECT | | | INJURY | | | | 4-AP DOSE | | |
|---|---|---|---|---|---|---|---|---|---|
| | | | | Frankel | | | mg per | Total | Total |
| Initials | Sex | Age | Level | Class | Years | Cause | 20 min. | (mg) | (mg/kg) |
| RB | M | 42 | T7/8 | A | 6.5 | Fall | 4 | 24 | 0.36 |
| SC | F | 39 | T7 | A | 10 | Unknown | 5 | 30 | 0.63 |
| HT* | F | 29 | C5 | B | 5.5 | Diving | 3 | 18 | 0.37 |
| LJ | M | 32 | C5 | B | 8.5 | Diving | 5 | 25 | 0.34 |
| EB* | F | 18 | C5 | C | 3.5 | Diving | 4 | 24 | 0.33 |
| GCh* | M | 44 | C5 | C | 5 | Construction | 5 | 33.5 | 0.53 |
| AW | M | 46 | T6 | D | 1.5 | Surgery | 5 | 25 | 0.26 |
| GCu | M | 65 | C4 | D | 9.5 | Sports | 3 | 18 | 0.22 |

*Received placebo in first trial. 4-AP in second
†Transverse myelitis of unknown origin

TABLE 2

Changes in neurological score at 2 hours after infusion of vehicle
(placebo) or 4-aminopyridine. The totals (across all tests) for
both negative (−ve) and positive (+ve) changes
in score for each patient are shown. The total possible
scores for each patent were 130 (motor) and 224 (sensory).

| | PLACEBO Change in Score* | | | | 4-AP Change in Score* | | | |
|---|---|---|---|---|---|---|---|---|
| | Motor | | Sensory | | Motor | | Sensory | |
| SUBJECT | −ve | +ve | −ve | +ve | −ve | +ve | −ve | +ve |
| RB | 0 | 0 | 0 | 0 | 0 | 0 | 0 | 0 |
| SC | 0 | 0 | 0 | 0 | 0 | 0 | 0 | 0 |
| HT | 0 | 0 | 0 | 0 | 0 | 0 | 0 | +3 |
| LJ | 0 | +1 | −9 | +3 | 0 | 0 | 0 | +2 |
| EB | 0 | +1 | 0 | 0 | 0 | +4 | −5 | +14 |
| GCh | 0 | 0 | 0 | 0 | 0 | +16 | 0 | +27 |
| AW | −2 | 0 | −7 | +2 | 0 | +4 | 0 | +20 |
| GCu | −4 | +1 | −11 | +6 | 0 | +2 | −2 | 0 |
| TOTAL | −6 | +3 | −27 | +11 | 0 | +26 | −7 | +66 |

*Ignoring half point assignments and excepting vibration sensation score (Table 3).

TABLE 3

Changes in total score for vibration sensation
at 2 hours after infusion of vehicle (placebo)
or 4-aminopyridine. The total possible score for each subject
was 32.

| | PLACEBO | | 4-AP | |
|---|---|---|---|---|
| SUBJECT | −ve | +ve | −ve | +ve |
| RB | 0 | 0 | 0 | 0 |
| SC | 0 | 0 | 0 | 0 |
| HT | 0 | 0 | −7 | +1 |
| LJ | 0 | +2 | 0 | 0 |
| EB | * | * | −4 | 0 |
| GCh | 0 | 0 | −2 | 0 |
| AW | −4 | 0 | 0 | 0 |
| GCu | −1 | +3 | 0 | 0 |
| TOTAL | −5 | +5 | −12 | +1 |

*Data not recorded.

TABLE 4

Changes in score for deep tendon reflexes at 2
hours after infusion of vehicle (placebo) or 4-
aminopyridine. The total possible score for each patient
was 32.

| | PLACEBO | | 4-AP | |
|---|---|---|---|---|
| SUBJECT | arms | legs | arms | legs |
| RB | 0 | +1 | +4 | +2 |
| SC | 0 | 0 | +4 | +1 |
| HT | * | 0 | +1 | −2 |
| LJ | +2 | 0 | * | * |
| EB | * | * | * | * |
| GCh | 0 | 0 | +4 | 0 |
| AW | 0 | 0 | * | +3 |
| GCu | 0 | −1 | 0 | −2 |
| TOTAL | +2 | 0 | +13 | +2 |

*Data not recorded.

REFERENCES

ARHEM, P. and JOHANSSON, S. (1989) A model for the fast 4-aminopyridine effects on amphibian myelinated nerve fibers. A study based on voltage clamp experiments. Acta Physiol. Scand. 137:53–61.

BERIC, A., DIMITRIJEVIC, M. R., and LINDBLOM, U. (1988) Central dysesthesia syndrome in spinal cord injury patients. Pain 34:109–116.

BERIC, A. (1990) Altered sensation and pain in spinal cord injury, in: Recent Achievements in Restorative Neurology 3. Altered Sensation and Pain. M. R. Dimitrijevic, P. D. Wall and U. Lindblom (eds). Karger: Basel, pp. 27–36.

BLIGHT, A. R. (1983a) Cellular morphology of chronic spinal cord injury in the cat: analysis of myelinated axons by line-sampling. Neuroscience. 10:521–543.

BLIGHT, A. R (1983b) Axonal physiology of chronic spinal cord injury in the cat: intracellular recording in vitro. Neuroscience. 10:1471–1486.

BLIGHT, A. R. and DECRESCITO, V. (1986) Morphometric analysis of experimental spinal cord injury in the cat: the relation of injury intensity to survival of myelinated axons. Neuroscience. 19:321–341.

BLIGHT, A. R. and GRUNER, J. A. (1987) Augmentation by 4-aminopyridine of vestibulospinal free fall responses in chronic spinal-injured cats. J. Neurol. Sci. 82:145–159.

BLIGHT, A. R. (1989) Effect of 4-aminopyridine on axonal conduction-block in chronic spinal cord injury. Brain Res. Bull. 22:47–52.

BLIGHT, A. R. (1991) Morphometric analysis of a model of spinal cord injury in guinea pigs, with behavioral evidence of delayed secondary pathology. J. Neurol. Sci. 103:156–171.

BLIGHT, A. R. TOOMBS, J. P., BAUER, M. S., and WIDMER, W. R. (1991) The effects of 4-aminopyridine on neurological deficits in chronic cases of traumatic spinal cord injury in dogs: a phase I clinical trial. J. Neurotrauma 8:103–119.

BOSTOCK, H., SEARS, T. A., and SHERRATT, R. M. (1981) The effects of 4-aminopyridine and tetraethylammonium ions on normal and demyelinated mammalian nerve fibres. J. Physiol. 313:301–315.

BOWE, C. M., KOCSIS, J. D., TARG, E. F., and WAXMAN, S. G. (1987) Physiological effects of 4-aminopyridine on demyelinated mammalian motor and sensory fibers. Ann. Neurol. 22:264–268.

BRESNAHAN, J. C., BEATTIE, M. S., TODD, F. D. III, and NOYES, D. H. (1987) A behavioral and anatomical analysis of spinal cord injury produced by a feedback-controlled impaction device. Exp. Neurol. 95:548–570.

CHANDY, K. G., DECOURSEY, T. E., CAHALAN, M. D., MCLAUGHLIN, C., and GUPTA, S. (1984) Voltage-gated potassium channels are required for human T lymphocyte activation. J.Exp.Med 160:369–385.

CHOQUET, D. and KORN, H. (1988) Modulation of voltage-dependent potassium channels in B-lymphocytes. Biochem. Pharmacol. 37:3797–3802.

DAVIS, F. A., STEFOSKI, D., and RUSH, J. (1990) Orally administered 4-aminopyridine improves clinical signs in multiple sclerosis. Ann. Neurol. 27:186–192.

DIMITRIJEVIC, M. M., DIMITRIJEVIC, M. R., ILLIS, L. S., NAKAJIMA, K., SHARKEY, P. C., and SHERWOOD, A. M. (1986a) Spinal cord stimulation for the control of spasticity in patients with chronic spinal cord injury: I. Clinical observations. Cent. Nerv. Syst. Trauma 3:129–144.

DIMITRIJEVIC, M. R., ILLIS, L. S., NAKAJIMA, K., SHARKEY, P. C., and SHERWOOD, A. M. (1986b) Spinal cord stimulation for the control of spasticity in patients with chronic spinal cord injury: II. Neurophysiologic observations. Cent. Nerv. Syst. Trauma 3:145–152.

EIDELBERG, E., STRAEHLEY, D.; ERSPAMER, R., and WATKINS, C. J. (1977) Relationship between residual hindlimb-assisted locomotion and surviving axons after incomplete spinal cord injuries. Exp. Neurol. 56:312–322.

EIDELBERG, E., STORY, J. L., WALDEN, J. G., and MEYER, B. L. (1981a) Anatomical correlates of return of locomotor function after partial spinal cord lesions in cats. Exp. Brain Res. 42:81–88.

EIDELBERG, E., WALDEN, J. G., and NGUYEN, L. H. (1981b) Locomotor control in macaque monkeys. Brain 104:647–663.

ELIASSON, S. G. MONAFO, W. W. (1991) Effects of 4-aminopyridine on protein phosphorylation in heat-blocked peripheral nerve. J. Neurol. Sci. 105:175–182.

EVENHUIS, J., AGOSTON, S., SALT, P. J., DELANGE, A. R., WOUTHUYSEN, W., and ERDMAN, W. (1981) Pharmacokinetics of 4-aminopyridine in human volunteers. Br. J. Anaesth. 53:567–570.

GLOVER, W. E. (1982) The aminopyridines. Gen. Pharmacol. 13:259–285.

HAYES, K. C., BLIGHT, A. R., ALLATT, R. D., et al (1991) Effects of intravenous 4-aminopyridine on neurological function in chronic spinal cord injured patients: preliminary observations. Proc. IBRO World Conf. Neurosci. p. 345.

ILLIS, L. S., READ, D. J., SEDGEWICK, E. M., and TALLIS, R. C. (1983) Spinal cord stimulation in the United Kingdom (Review). J. Neurol. Neurosurg. Psychiat. 46:299–304.

JACK, J. J. B., REDMAN, S. J., and WONG, K. (1981) Modifications to synaptic transmission at group Ia synapses on cat spinal motoneurones by 4-aminopyridine. J. Physiol. 321: 111–126.

JACOBS, M. J., JORNING, P. J., BECKERS, R. C., et al (1990) Foot salvage and improvement of microvascular blood flow as a result of epidural spinal cord electrical stimulation. J. Vasc. Surg. 12:354–360.

JANKOWSKA, E., LUNDBERG, A., RUDOMIN, P., and SYKOVA, E. (1977) Effects of 4-aminopyridine on transmission in excitatory and inhibitory synapses in the spinal cord. Brain Res. 136:387–392.

JANKOWSKA, E., LUNDBERG, A., RUDOMIN, P., and SYKOVA, E. (1982) Effects of 4-aminopyridine on synaptic transmission in the cat spinal cord. Brain Res. 240:117–129.

JELLINGER, K. (1976) Neuropathology of cord injuries, in: Handbook of Clinical Neurology, Vol 25, Part I, Injuries of the Spine and Spinal Cord. P. J. Vincken, G. W. Bruyn and R. Braakman (eds). North Holland: Amsterdam, pp. 43–121.

JOSEPHSON, I. R., SANCHEZ-CHAPULA, J., and BROWN, A. M. (1984) Early outward current in rat single ventricular cells. Circ. Res. 54:157–162.

KAKULAS, B. A. (1984) Pathology of spinal injuries. Cent. Nerv. Syst. Trauma 1:117–129.

KAKULAS, B. A., SMITH, E., GAEKWAD, U., KAELAN, C., and JACOBSEN, P. F. (1990) The neuropathology of pain and abnormal sensations in human spinal cord injury derived from the clinicopathological data base at the Royal Perth Hospital, in: Recent Achievements in Restorative Neurology, 3: Altered Sensation and Pain. M. R. Dimitrijevic, P. D. Wall and U. Lindblom (eds). Karger-:Basel, pp. 37–41.

KAKULAS, B. A. and BEDBROOK, G. M. (1969) A correlative clinicoathologic study of spinal cord injury. Proc. Aust. Assoc. Neurologists 6:123–132.

KIRCHHOFF, C., LEAH, J. D., JUNG, S., and REEH, P. W. (1992) Excitation of cutaneous sensory nerve endings in the rat by 4-aminopyridine and tetraethylammonium J. neurophysiol. 67:125–131.

KOCSIS, J. D., MALENKA, R. C., and WAXMAN, S. G. (1983) Effects of extracellular potassium concentration on the excitability of the parallel fibres of the rat cerebellum. J. Physiol. (Lond) 334:225–244.

KOCSIS, J. D., BOWE, C. M., and WAXMAN, S. G. (1986) Different effects of 4-aminopyridine on sensory and motor fibers: pathogenesis of paresthesias. Neurology 36: 117–120.

KOSTKA, P., HANSEBOUT, R., and GUPTA, R. N. (1992) Column liquid chromatographic determination of 4-aminopyridine in plasma and urine after derivatization with benzoyl chloride. Clin. Biochem. 25:144.

LEMEIGNAN, M. (1972) Analysis of the action of 4-aminopyridine on the cat lumbar spinal cord. 1. Modification of the afferent volley, the monosynaptic discharge amplitude and the polysynaptic evoked responses. Neuropharm. 11:551–558.

LINDEROTH, B., FEDORCSAK, I., and MEYERSON, B. A. (1991) Peripheral vasodilation after spinal cord stimulation: animal studies of putative effector mechanisms. Neurosurgery 28:187–195.

LLINAS, R., WALTON, K., SUGIMORI, M., and SIMON, S. (1982) 3- and 4-aminopyridine in synaptic transmission at the squid giant synapse, in: Aminopyridines and Similarly Acting Drugs: Effects on nerves, Muscles and Synapses. P. Lechat, S. Thesleff and W. C. Bowman (eds). Pergamon Press: Oxford, pp. 69–79.

MARCHAND, S., BUSHNELL M. C., MOLINA-NEGRO, P., MARTINEZ, S. N., and DUNCAN, G. H. (1991) The effects of dorsal column stimulation on measures of clinical and experimental pain in man. Pain 45:249–257.

MEGLIO, M., CIONI, B., and SANDRIC, S. (1981) Spinal cord stimulation and peripheral blood flow: Part 1, in: Indications for Spinal Cord Stimulation. Y. Hosobuchi and T. Corbin (eds). Excerpta medica: Amsterdam, pp. 60–66.

MOLGO, J. (1982) Effects of aminopyridines on neuromuscular transmission, in: Aminopyridines and Similarly Acting Drugs: Effects on Nerves, Muscles and Synapses. P. Lechat, S. Thesleff and W. C. Bowman (eds). Pergamon Press: Oxford, pp. 95–116.

NOBLE, L. J. and WRATHALL, J. R. (1989) Correlative analyses of lesion development and functional status after graded spinal cord contusive injuries in the rat. Expl. Neurol. 103:34–40.

NOORDENBOS, W. and WALL, P. D. (1976) Diverse sensory functions with an almost totally divided spinal cord. A case of spinal cord transection with preservation of part of one anterolateral quadrant. Pain 2:185–195.

OCHOA, J. (1982) Pain in local nerve lesions, in: Abnormal Nerves and Muscles as Impulse Generators. W. I. Culp and J. Ochoa (eds). Oxford University Press: New York, pp. 568–587.

SAADÉ, N., JABBUR, S. J., and WALL, P. D. (1985) Effects of 4-aminopyridine, GABA and bicuculline on cutaneous receptive fields of cat dorsal horn neurons. Brain Res. 344: 356–359.

SAADÉ, N. E., BANNA, N. R., KHOURY, A., LABBUR, S. J., and WALL, P. D. (1982) Cutaneous receptive field alterations induced by 4-aminopyridine. Brain Res. 232: 177–180.

SEGAL, J. L., BRUNNEMANN, S. H., ELTORAI, I. M. and VULPE, M. (1991) Decreased systemic clearance of lorazepam in humans with spinal cord injury. J. Clin. Pharmacol. 31:651–656.

SEMBA, K., GELLER, H. M., and EGGER, M. D. (1985) 4-aminopyridine induces expansion of cutaneous receptive fields of dorsal horn cells. Brain Res. 343:398–402.

SHEALY, C. N., MORTIMER, J. T., and RESWICK, J. (1967) Electrical inhibition of pain by stimulation of the dorsal columns: preliminary clinical report. Anesth. Analg. 46: 489.

SMITH, K. J. and MCDONALD, W. I. (1982) Spontaneous and evoked electrical discharges from a central demyelinating lesion. J. Neurol. Sci. 55:39–47.

STEFOSKI, D., DAVIS, F. A., FAUT, M., and SCHAUF, C. L. (1987) 4-Aminopyridine improves clinical signs in multiple sclerosis. Ann. Neurol. 21:71–77.

STEFOSKI, D., DAVIS, F. A., FITZSIMMONS, W. E., LUSKIN S. S., RUSH, J., and PARKURST, G. W. (1991) 4-Aminopyridine in multiple sclerosis: Prolonged administration. Neurology 41:1344–1348.

TAPIA, R., SITGES, M., and MORALES, E. (1985) Mechanism of the calcium-dependent stimulation of transmitter release by 4-aminopyridine in synaptosomes. Brain Res. 361:373–382.

TARG, E. F. and KOCSIS, J. D. (1985) 4-Aminopyridine leads to restoration of conduction in demyelinated rat sciatic nerve. Brain res. 328: 358–361.

TARG, E. F. and KOCSIS, J. D. (1986) Action potential characteristics of demyelinated rat sciatic nerve following application of 4-aminopyridine. Brain Res. 363:1–9.

TASKER, R. R. (1990) Pain resulting from central nervous system pathology (central pain), in: The Management of Pain, Vol 1., J. J. Bonica (ed). Lea and Febiger: Philadelphia, pp. 264–283.

THESLEFF, S. (1980) Aminopyridines and synaptic transmission. Neuroscience 5:1413–1419.

UGES, D. R. A. and HUIZINGA, T. (1981) 4-Aminopyridine: Analysis of the substance and a method for the preparation of a solution for injection in man. Pharm. Acta Helv. 56: 158–162.

UGES, D. R. A., SOHN, Y. J., GREIJDANUS, B., SCAF, A. H. J., and AGOSTON, S. (1982) 4-Aminopyridine kinetics. Clin. Pharmacol. Ther. 31: 587–593.

WAGONER, P. K. and OXFORD, G. S. (1990) Aminopyridines block an inactivating potassium current having slow recovery kinetics. Biophys. J. 58:1481–1489.

WAXMAN, S. G. and WOOD S. L. (1984) Impulse conduction in inhomogeneous axons: effects of variation in voltage-sensitive ionic conductances on invasion of demyelinated axon segments and preterminal fibers. Brain Res. 294:111–122.

WAXMAN, S. G., KOCSIS, J. D., and ENG, D. L. (1985) Ligature-induced injury in peripheral nerve: electrophysiological observations on changes in action potential characteristics following blockade of potassium conductance. Muscl. Nerve 8:85–92.

XU, X.-J., HAO, J.-X., ALDSKOGIUS, H., SEIGER, A., and WIESENFELD-HALLIN, Z. (1992) Chronic pain-related syndrome in rats after ischeimic spinal cord lesion: a possible animal model for pain in patients with spinal cord injury: Pain 48:279–290.

YEH, J. Z., OXFORD, G. S., WU, C. H. and NARAHASHI, T. (1976a) Interactions of aminopyridines with potassium channels of squid axon membranes. Biophys. J. 16:77–81.

YEH, J. Z., OXFORD, G. S., WU, C. H. and NARAHASHI, T. (1976b) Dynamics of aminopyridine block of potassium channels in squid axon membrane. J. Gen. Physiol. 68: 5195–535.

The embodiments of the invention in which an exclusive property or privilege is claimed are defined as follows:

1. A method of reducing chronic pain and spasticity in a spinal cord injured patient in need of such treatment comprising administering an effective amount of 4-aminopyridine to said patient.

2. A method according to claim 1 wherein said administering step comprises administering 4-aminopyridine in a dose of about 15–30 mg.

3. A method according to claim 1 wherein said administering step comprises administering 4-aminopyridine intravenously.

4. A method of treating chronic pain in a spinal cord injured patient in need of such treatment comprising administering a pain-reducing amount of 4-aminopyridine to said patient.

5. A method of reducing spasticity in a spinal cord injured patient in need of such treatment comprising administering a spasticity reducing amount of 4-aminopyridine to said patient.

* * * * *